United States Patent [19]

Smith, executor et al.

[11] 4,219,395
[45] Aug. 26, 1980

[54] ELECTROCHEMICAL FRACTIONATION PROCESS

[76] Inventor: Maryanne Smith, deceased, late of Santa Monica, Calif., by Arthur C. Smith, 624 Alta Ave., Santa Monica, Calif. 90402 executor

[21] Appl. No.: 230,083

[22] Filed: Feb. 28, 1972

Related U.S. Application Data

[63] Continuation of Ser. No. 848,056, Aug. 6, 1969, abandoned.

[51] Int. Cl.$^2$ ............... G01N 27/26; B03C 5/00; C25B 7/00
[52] U.S. Cl. ............... 204/180 R; 204/299 R
[58] Field of Search ............... 204/180 R, 299, 106, 204/112

[56] References Cited

U.S. PATENT DOCUMENTS

| | | | |
|---|---|---|---|
| 2,535,395 | 12/1950 | Dinsley | 204/299 |
| 2,566,308 | 9/1951 | Brewer | 204/180 R |
| 2,762,254 | 9/1956 | Kegeles | 204/180 R |
| 3,042,597 | 7/1962 | Schumacher | 204/180 R |
| 3,127,336 | 3/1964 | Chemla | 204/180 R |

OTHER PUBLICATIONS

Nancollas, "Interactions in Electrolyte Solutions", p. 169, (1966).
McDonald, "Ionography", pp. 178-181, (1955).
Freyer & Wagener, "Electrochemical Processes . . . Isotopes", pp. 757-766 of Angen. Chem. Internat. Edit. vol. 6, No. 9, (1967).
Cawley, "Electrophoresis and Immunoelectrophoresis", pp. 5 & 6, Little, Brown & Co. Publishers, (1969).

Primary Examiner—Arthur C. Prescott

[57] ABSTRACT

The present invention is a novel electrochemical process for separating and/or purifying the components of mixed materials such as alloys, rare earths, spent reactor fuel rods, isotopes, or other normally difficult to separate materials which carry the same sign of the ionic charge when in solution (positive, negative or neutral), but which can be made to exhibit a difference in oxidation potential, comprising (a) passing a current through an electrolyte containing the dissolved materials to be separated (separants), carrier-formers and a solvent and (b) refluxing the separants, until the desired degree of purity is reached. The carrier-formers, which may carry a positive, negative or neutral charge, are capable of interacting with the separants to form separant-carriers such that for each separant there is at least one separant-carrier having a positive charge and one separant-carrier having a negative charge, such that each separant is divided between a pair of oppositely directed carriers.

6 Claims, 5 Drawing Figures

ELECTROCHEMICAL FRACTIONATION PROCESS

This application is a continuation of application Ser. No. 848,056, filed Aug. 6, 1969, now abandoned.

BACKGROUND OF THE INVENTION

This invention relates to purification processes and, more particularly, to a process for separating chemical species exhibiting, or capable of exhibiting, a difference in oxidation potential in solution.

At present, a number of electrochemical processes are employed to separate or purify materials, such as elemental metals and isotopes. Presently-employed electrochemical processes include electrolytic refining, electromigration, electrophoresis, electrodialysis, and other more limited techniques. In general, use of these methods is limited because of particular process requirements. Additionally, separation of some species by these methods can be so expensive due to high electrical power requirements that such separation is rendered impractical.

Electrolytic refining relies upon a difference in the oxidation potential of the species to be separated and upon electrochemical action at the electrodes to produce a desired separation. A limitation of this method is that the oxidation potentials must be substantially different to obtain significant separation.

Electromigration relies upon a difference in the migration velocity of similarly-charged species towards one of the electrodes. Fluid is flowed countercurrently to the species at a velocity intermediate that of the species to reverse the direction of one species. The disadvantage of this method is that very careful adjustments of the velocity of the counterflowing fluid must be continuously maintained and the nature of viscosity prohibits a constant and uniform flow across the cell. Furthermore, this method cannot be employed to separate species having substantially the same migration velocities and, for practical purposes, cannot be used to separate species having similar migration velocities.

Electrophoresis requires that the materials to be separated be such that they can be given charges opposite to each other and thus diverted to opposite electrodes. This method is most used in the drug industry for separating molecules that are capable of reacting with both acids and bases because their charges can be readily altered by, e.g., pH adjustment. This method cannot be employed where the materials to be separated cannot be oppositely directed by concentration or pH changes.

Electrodialysis separates by employing a physical barrier such as a membrane which preferentially passes one of the species to be separated. The disadvantage of this process is that membranes are not available to separate some species because of their similarity and, even when available, can be expensive to produce.

Other, more limited electrolytic techniques for isotope separation include preferential reduction methods used to produce heavy hydrogen by enrichment of the same over "light" hydrogen. This method requires that the reduction rate of one material be faster than that of the other material.

A uranium isotope process employing a similar sounding but quite different mechanism is described in U.S. Pat. No. 2,813,064 of A. Clark. This process employs uranous and uranyl ions which both normally flow toward the cathode. A counterflowing solution is employed to sweep the slower-flowing uranyl ions back to the anode. Because of an inherent preferential reduction and oxidation of the different uranium isotopes at the electrodes between uranous and uranyl ions, an isotope separation is produced. This process is very expensive and requires an extremely long time, e.g., 1400 hr. to effect an enrichment from 0.7111% to 0.7171%.

SUMMARY OF THE INVENTION

This invention is an electrochemical process for separating two or more dissolved materials to be separated (separants) which exhibit or which can be made to exhibit a difference in oxidation potential. Separation is effected by the use of carrier-formers which, with the separants, form separant-carriers and which also can show a different affinity for the separants causing some or all of the oxidation potential differences exhibited between carrier pairs. The overall reaction for a typical pair of separants may be described in the following symbolic language:

$$Cm + An \rightleftarrows Cn + Am$$

where m and n are separants and C and A designate carriers, mnemonically indicating net movement of the separant-carriers, e.g., Cm and An, toward the cathode and anode, respectively. Thus, e.g., Cm designates the form in which the average velocity of separant m is toward the cathode.

For each separant, one of the carriers so formed moves in a direction opposite to that of the other member of the carrier pair under the influence of an electrical field. Additionally, the carrier-formers are selected so that the separant-carriers rapidly and continuously interchange separants with an accompanying interchange in oxidation state of the separants. To effect separation by the method of this invention, carrier-formers and separant concentrations are selected so that for any two separants being separated, the ratio of the flux ratio of the separants (regardless of form) moving in one direction to the flux ratio of the separants moving in the opposite direction is not equal to one. That is, for the system described by the above symbolic equation, carrier-formers and separant concentrations are selected so that $$\frac{V_{Cn}[Cn]}{V_{Cm}[Cm]} \cdot \frac{V_{Am}[Am]}{V_{An}[An]} \neq 1$$

where $V_{Cn}[Cn]$ is the flux of separant n (regardless of form) in the cathode direction; $V_{Cn}$ is the average weighted migration velocity of Cn; and $[Cn]$ is the concentration of the separant n in the form Cn. $V_{Cm}[Cm]$, $V_{Am}[Am]$ and $V_{An}[An]$ have similar meanings with respect to Cm, Am and An, respectively.

The use of carrier-formers as described produces charged particles in two countercurrently-flowing streams each of which carries all separants and between which the separants are continuously interchanged. This interchange of separants between oppositely-flowing particle streams when combined with the preferential distribution of separants between carrier-formers results in each separant being given a net movement in a direction opposite to at least one of the other separants. This overall net movement of the separants in opposite directions effects a separation of the separants.

The separation produced as the carrier flux travels the length of the electrolytic cell is substantially increased by refluxing the separants. When the desired degree of separation or purification has been attained, the product separants are removed from the cell. The process may be operated continuously or as a batch process.

Separation is provided by the aforementioned interchange between counterflowing particle streams. Fluid flow, whether forced or due to convection, can degrade by remixing to such an extent that little or no separation takes place. Therefore, fluid flow is minimized and, in certain cases, may be eliminated, e.g., when using a gel.

This invention differs from electrophoresis because it uses reflux and a two-carrier system and, because of these differences, it is millions of times more selective and can separate materials that cannot be separated by electrophoresis. That is, this invention separates materials, say m and n, (considered two at a time, but allowing the simultaneous separation of more than two materials) by partitioning the separants between carriers designated A and C. The A carriers transport separants to the anode, and the C carriers transport separants to the cathode. Throughout the column (inter-electrode path) containing the separant-carriers, the separants are constantly being repartitioned between the carriers. In operation, oxidation takes place at the anode end and is transported toward the cathode by C with the separant-carrier flux towards the cathode becoming a progressively weaker oxidizing-agent as it reacts with the separant-carrier flux coming from the cathode and carrying reduced species. The effect is that the oxidation potential becomes graduated between the electrodes with the lowest oxidation potential located at the anode end, and the highest oxidation potential at the cathode end (materials more difficult to oxidize than hydrogen have negative oxidation potentials). The driving force for separation is the flow of oxidation-reduction potential in a fashion analogous to the flow of thermodynamic potential in a fractional distillation column. That is, if there are two or more separants with a pair of carriers for each separant and a reaction between each separant-carrier pair that will reach equilibrium in a time that is short compared to the time it takes for a separant-carrier to travel the length of the column, then when current is passed through the column, the system progresses towards a final state in which the separants become ordered along the column in the same order as their oxidation potentials with the strongest oxidizing material adjacent to the anode.

The advantages obtained from using this process are many. This process can separate very similar separants which bear the same charge in solution and which would otherwise migrate through the electrolytic cell at the same velocities. The use of carrier-formers herein effects a net reversal in direction of one of the separants to produce the desired separation. This process can also be employed to separate neutral or non-ionic separants from each other by similarly partitioning them between pairs of oppositely-charged carrier-formers.

The exchange reaction between the separant-carriers need not involve a change in oxidation number of the separants, but only a change in oxidation state. Many separants which have only one oxidation number in solution still exhibit a difference in electrode potential when combined with the carrier-formers of this invention. Thus, e.g., mixed isotopes or mixed elements having the same oxidation number in both flux streams can be readily separated by this process.

This process is highly efficient and requires only very short path lengths between electrodes, e.g., a millimeter or less when separating material with a moderate oxidation potential difference. For such, the length of the cell is presently limited only by the manufacturer's ability to construct it as small as it can be made. This small size means that the power requirements are low since expended power is directly related to the cell length and this, in turn, means relatively inexpensive operation. Operating cost is also low because the time required to attain high degrees of separation is low, e.g., a few hours or less to achieve the same degree of separation that required over 1000 hours by the A. Clark method.

Extreme degrees of purity can be obtained using this process. For example, products which are 99.999% free of the removed materials can be produced in one stage. It is only a matter of allowing the requisite time which, as aforementioned, is relatively short.

A further advantage is that this process can be employed with solutions fixed in position by gels. It is only necessary that the separant-carriers be able to migrate through the electrolytic medium.

DESCRIPTION OF THE PREFERRED EMBODIMENT

Figure 1:
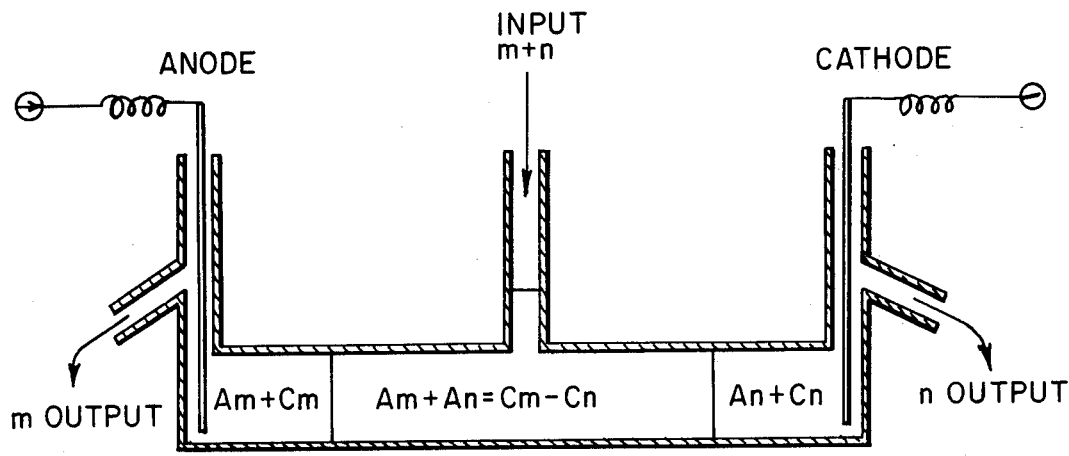
FIG. 1 is a cross-sectional view of an electrolytic cell illustrating the distribution of separant forms along the length of the cell.

The process of this invention is an electrolytic process which can effectively separate species (herein and in the claims referred to as "separants") which exhibit a difference in standard state oxidation potential or which can be made to exhibit such a difference by addition thereto of selected ligands. Advantage is taken of this difference in oxidation potential by employing ionic ligands to form carriers that show a preference, based on oxidation potential differences, for one set of species to be separated from another and cause the separants to have a net migration in opposite directions. The following description will be in terms of a typical separant pair for ease of description, but it applies equally to mixtures containing more than two separants. Due to the interaction between the separants and the ionic ligands or carrier-forming agents, two intimately-mixed, counter-currently-flowing, particle streams are formed, between which there is an interchange of the separants, with each interchange being accompanied by an oxidation state change and by a simultaneous change in the direction of each separant. With increasing transit, one of the particle streams is enriched in one of the separants and the other, oppositely-flowing stream is enriched in the other separant.

An electrical source is employed to provide the motive force necessary to move the particles. The same or another energy source is employed to transfer separants from one carrier stream to the other at or near the ends so that they are returned for reflux through the reaction zone for further interaction and separation. Of course, reflux and direction reversals of the separant particles occur continuously throughout the reaction zone.

Separation by the method of this invention requires only particle flow or migration. That is, fluid flow is not required to effect separation. Furthermore, fluid flow is minimized since, if too strong, it can essentially prevent or severely degrade separation by this invention. In some cases, e.g., by carrying out separation in a gel, fluid flow can be eliminated. This is a distinct advantage over electromigration separation processes.

In general, the species to be separated or separants are dissolved in a solvent contained in an electrolytic cell. Under the influence of a voltage applied to the cell electrodes, all separants, unless neutral, would migrate toward either the anode or the cathode. Carrier-forming ligands are added to the cell to interact with the separants in a manner such that the reaction between the resulting separant-carriers causes one of the separants to be given a preferred or net movement toward one electrode and causes the other separant to be given an overall movement toward the other electrode, thereby effecting a separation of the separants. To provide almost 100% separation, the separant-carrier streams reaching the ends of the electrolytic cell are turned around by oxidation at or near one electrode and by reduction at or near the other electrode to thereby cause the separants to reflux and obtain the benefits of continuous interchange throughout the length of the cell.

Each separant is present in this process in at least two carrier forms—one that has net drift toward the cathode and the other that has net drift toward the anode when an electric field is applied. A difference in oxidation potential exists between any two separant pairs in their two forms so that any exchange reaction between separant-carrier pairs is accompanied by an energy change. The carrier-formers react with each separant to produce at least one separant-carrier having a migration direction toward the cathode and at least one separant-carrier having a migration direction toward the anode. Each separant thereby migrates or is carried in both directions and the direction in which a separant particle moves at any particular time depends upon the form which it is in at that time. Thus, as each separant particle alternates between its two, oppositely-moving forms, it continuously reverses its direction with the resident time in either carrier stream related to the energy difference in the exchange reaction. That is, because the energy change involved in separant-carrier interchange causes the streams to exhibit a preference for one of the separants, the net movement of each separant is in a direction opposite to that of the other separant.

The carrier-formers are also selected so that there is a continuous rapid interchange of separants between the various forms (separant-carriers) in which the separants appear so that the time to reach equilibrium is very short compared to the time it would take for a particle to travel the cell length. When the carrier-formers are employed in particular concentrations, as will be described hereafter, the result is that two countercurrently-flowing streams of charged particles are produced in the electrolytic cell and the particles are rapidly interchanged between these streams. Both separants exist in each of these intimately-mixed, countercurrently-flowing particle streams. As the aforementioned interchange takes place, each stream is always slightly richer in one of the separants, and slightly depleted in the other, compared to the other stream at the same point, so that separation is effected by transit of the carriers through the cell. To ensure that this separation occurs, appropriate carrier-formers are selected and the concentrations of the various separant forms are adjusted so that the ratio of the flux ratio of the separants (regardless of their form) moving in one direction to the flux ratio of the separants moving in the other direction is not equal to one.

Turning now to the constituents employed in this process, including the components separated by this process, the latter will first be described. The separants may be almost any materials regardless of whether they are normally ionic in solution provided they exhibit or can be made to exhibit a difference in oxidation potential, and regardless of whether they undergo a change in oxidation number. It is only necessary that carrier-formers be available such that each separant can be partitioned between pairs of oppositely migrating carriers, and such that there is a difference in oxidation potential between pairs. Thus, e.g., neutral bromine ($Br_2$) can be partitioned between oppositely-directed carriers in a solution of potassium bromide (KBr) and sodium sulfate ($Na_2SO_4$) since it divides itself between $Br_3$—ions and an unidentified, positive separant-carrier which is known to exist because of the large observable migration velocity of bromine towards the cathode and because of the observation of a sharp interface between the dark brown $Br_3$— and a colorless sulfate solution.

The process of this invention is particularly useful for separating separants that are normally positive ions in solution from each other although separants that are normally negative ions or non-ionic when in solution may also be separated from each other with equal ease. Examples of separants which can be separated from each other are: different elements such as cobalt from nickel and iron, vanadium from uranium, silver from copper, sodium from potassium, and bromine from iodine; isotopes such as $K^{39}$ from $K^{41}$, uranium isotopes and other isotopes from spent reactor fuel; organic compounds such as the amino acids and sugars; and rare earths such as the components of misch metal.

As will be noted from the foregoing examples, it is not necessary that each separant be able to exhibit a difference in oxidation number while in solution. It is only necessary that each exhibit or can be made to exhibit a difference in oxidation or electrode potential. This can be accomplished by selection of carrier-formers which alter the oxidation potential of the separants. Thus, separants having a single oxidation state in aqueous solution, such as sodium and potassium, can be separated by addition thereto of carrier-formers, e.g., trimetaphosphate and methanol which alter the electrode potential of the separants.

More specifically, the process of this invention is capable of separating separants which take part in electron exchange or in ion exchange reactions. The latter is sometimes referred to herein as isoelectric stagnation. In the electron exchange reactions, each of the separants is present in two oxidation states which differ in oxidation number. For example, in the separation of iron from copper, the iron is present in both ferrous and ferric forms and the copper is present in both cuprous and cupric forms. Electron gain or loss by the iron forms is accompanied by electron loss or gain, respectively, by the copper forms during reaction between iron and copper separant-carriers. In contrast, the ion exchange separations are between separants which exhibit only one oxidation number during the separation but which are each present in two forms which exhibit an oxidation potential difference due to their combination with the carrier-formers employed herein. This type of separation is characterized by the separation of sodium and potassium which have only one oxidation state. Combination of, e.g., the sodium, with the carrier-former(s) produces two forms of sodium ion, e.g., one being elemental sodium ion and the other being sodium ion combined with a carrier-former, which differ from each other in electrode potential. The same is true for the potassium. Ion exchange reactions may also take place with separants which, in one environment, could exhibit different oxidation numbers, e.g., iron or copper, but which, in another environment, employ only a single oxidation number.

Separant oxidation states which are normally unstable in aqueous solution may still be employed if they can form stable complexes in solution with the carrier-formers. For example, cuprous ions are unstable in water in that they disproportionate into cupric ions and metallic copper. However, their soluble complexes, e.g., cuprous bromide complexes, are quite stable.

The carrier-formers will be next described. As used herein, the term "carrier-former" designates any material which, when acting in concert with one or more other carrier-formers, causes a portion of a separant to acquire an average ionic charge such that it will be carried towards one of the electrodes in the electrolytic cell. A separant acted on by, or reacted with, a carrier-former is transformed into one or a group of separant-carriers. A "carrier-former" may be as simple as a solvent that permits ionization of ionic salt to thereby form a simple separant-carrier. For example, a separant such as potassium (K) has soluble salts that dissolve in water or liquid ammonia to produce the cathode directed separant-carrier potassium ion ($K^+$). Or, a carrier-former may be simple but form a group of various complexes containing ions of both signs as well as neutral species. For example, a separant such as copper in the cupric state reacts with a carrier-former such as bromide ion ($Br^-$) to form several separant-carriers, e.g., $CuBr_3^-$, $CuBr_2$, $CuBr_4^-$ and $CuBr^+$. The term "carrier" is employed herein to collectively designate any group of separant-carriers that has an average motion that carries a portion of a particular separant towards either of the electrodes. A carrier pair is formed for each separant with one carrier carrying a portion of the separant toward one electrode under the influence of an electric field while permitting another portion of the same separant to be simultaneously transported to the opposite electrode also due to action of the electric field. For example, for a system in which iron is one of the separants and bromide ion and water are the carrier-formers, ferrous bromide complexes form a carrier system at the correct concentration of bromide ion which provides ferrous ions with a net movement toward the anode, while simultaneously giving ferric iron an average net movement toward the cathode.

The carrier-formers include any materials, whether positively-charged, negatively-charged or neutral when in solution, which are capable of reacting with the separants to provide the latter with one of the oppositely-directed, carrier pairs. The carrier-formers may also be materials which show a preference for one separant over another which thereby causes an additional oxidation potential difference. For separants with a single oxidation number, carrier-formers must have a preference for one separant over another, as this is the only source of a potential difference. Oppositely-directed, separant-carriers must be capable of rapidly reacting with each other such that after an exchange reaction, the separants have changed directions.

The number of different carrier-formers employed depends upon the nature of the separants in solution and upon the particular oxidation states exchanged. For some separants that ionize in the solvent, only one carrier-former in addition to the solvent need be employed to form a carrier pair since the separant, in ionized form, already has a directional movement in an electric field and it is only necessary to employ one additional carrier-former (although more than one may be employed) to give a portion of the separant movement in the opposite direction. However, if a separant, e.g., sugar, does not ionize in a particular solvent, e.g., water, at least two carrier-formers must be added to the solvent to produce a carrier pair moving in opposite directions under the influence of an electric field. The foregoing applies for each separant, although the same carrier-former(s) employed to provide a separant with the requisite directional movement may also provide a second separant with the requisite movement.

The selected set of carrier-formers should provide the most oxidized form of the separant with an overall movement toward the cathode so that it can be reduced there and returned for reflux and should provide the least oxidized form of the separant with an overall movement toward the anode. However, when the oxidation-reduction function of the physical electrodes is replaced by interface electrodes, as will be described hereafter, the most oxidized form of the separant can be directed toward the anode and the least oxidized form of the separant can be directed toward the cathode.

Herein, the terms "oxidation" and "reduction" are used in the general sense, i.e., if a material reacts with an oxidizing/reducing agent, the material is considered to be oxidized/reduced and the agent is thereby reduced/oxidized. If the reaction is electron exchange, the lowest oxidation state of a separant has the lowest oxidation number, e.g., $Fe^{++}$ in a ferrous-ferric system. If the reaction is ion exchange, the lowest oxidation state of a separant has the lowest oxidation potential, e.g., $Fe^{+++} + 4Br^- \rightleftharpoons FeBr_4^{--}$ or $Zn^{++} + 4Br^- \rightleftharpoons ZnBr_4^{--}$ where the elemental forms of the separants (iron or zinc) differ in oxidation potential from the iron and zinc in their bound forms.

The carrier-formers employed herein can exhibit a preference for one separant over another causing an oxidation potential difference between the separants. This preference basis can be improved by employing especially-selected chelating agents. The latter exhibit a preference based upon the additional factor of a separant's atomic or molecular size. By increasing the preference of a carrier-former for one separant over another in this manner, the oxidation state difference between the separants is increased. Examples of useful strongly-selective chelating centers include the porphin end of chlorophyll or hemoglobin and phthalocyanine.

Separation by the process of this invention takes place in solution. The solvent is any liquid in which the separant-carriers are soluble and which permits ionization of the separant-carriers. The solution may be held in the form of a gel. Examples of solvents usable in this invention include, e.g., water, methanol, ethanol, ammonia, dioxane, and dimethyl formamide. Combinations of solvents may also be employed.

The solvent itself may also act as a carrier-former. Water and dimethylformamide are examples of solvents which may also act as neutral carrier-formers. The solvent with dissolved separant-carriers is collectively referred to as the "electrolyte".

The motive force for the carriers is electrical. Current is passed through the electrolyte between electrodes extending into the electrolyte. The electrodes may be inert or not, depending upon the particular separation. If the electrodes employed are inert, platinum electrodes are preferred although graphite will work even though it slowly disintegrates for many anode electrode reactions. Although not inert, copper and silver are adequate for many cathode reactions.

Because of the prevalence of metallic separants requiring separation and for clarity of description, the process of this invention will first be more particularly described with reference to the separation of pairs of separants in a positive oxidation state. Process differences relating to the separation of negative and neutral oxidation states of the separants will be described thereafter. Unless otherwise stated, the most oxidized form of a separant migrates toward the cathode and the least oxidized form migrates toward the anode.

Considering now the separation of separants m and n, the interchange reaction between the separant-carriers for this process is symbolically shown in equation (1):

$$Cm + An \rightleftharpoons Am + Cn \tag{1}$$

where Cm designates separant m in the carrier form in which m moves toward the cathode;

An designates separant n in the carrier form in which it moves toward the anode;

Am designates separant m in the carrier form in which it moves toward the anode; and Cn designates separant n in the carrier form in which it moves toward the cathode.

An electrolytic cell illustrating the foregoing is shown in FIG. 1. As shown therein, the separants in their various forms are present in a central separation zone defined by concentration interfaces which will be described hereafter. On the physical electrode side of each interface, there is shown one of the separants in its various forms indicating that separation has taken place.

The object of forming carrier pairs is to obtain two intimately-mixed, counter-flowing streams. One stream flows toward the cathode and comprises both separants m and n as the forms Cm and Cn. The other stream flows toward the anode and comprises both separants m and n as the forms Am and An. However, although each separant is present in both counter-flowing streams, a separant, as it appears, in one stream, differs in form from itself, as it appears in the other stream, and this difference manifests itself in a difference in oxidation state. For example, a separant such as iron in an aqueous, ethanolamine system wherein bromide is the ionic carrier-former may be present in all of the following separant-carrier forms: $Fe^{2+}$, $Fe^{3+}$, $FeBr_3^-$, $FeBr_4^-$ and other complexes. Although the ferrous ($Fe^{2+}$) and ferric ($Fe^{3+}$) ions normally migrate toward a cathode, the effect of the carrier-formers is such that the average drift velocity of ferric iron is toward one electrode (cathode) and the average drift velocity of ferrous iron is toward the other electrode (anode). Thus, the carrier stream for ferrous iron includes $Fe^{2+}$ and $FeBr_3^-$ (and other ferrous complexes) and the carrier stream for ferric iron includes $Fe^{3+}$ and $FeBr_4^-$ (and other ferric complexes). Overall, the iron will be given a net movement in one direction which will be opposite to the net directional movement of another separant from which the iron is to be separated. The overall direction of the iron is determined by the relative oxidation potential of the other separant pair. A separant more difficult to oxidize than ferrous to ferric in the prevailing environment will cause iron to move toward the cathode and vice versa.

In addition to the presence of both separants in both streams simultaneously, there is a continuous interchange of separants m and n between the two streams as described by equation (1). For example, separant m in the form Cm reacts with separant n in the form An so that the former is changed into the form Am which will move in a direction opposite to the Cm form. Additionally, separant m in its Am form is continuously changed back to its Cm form by reaction with Cn which restores separant n to its previous An form. The exchange reaction may be charge exchange, or ion exchange, or both. Therefore, each separant particle will move in one carrier form toward one electrode, interact according to equation (1) to thereby be transferred to its other carrier form, change its direction of movement when in this other form, re-react according to equation (1) to thereby revert to its first form with accompanying directional change, and so on until it reaches one of the electrodes. Each interchange is accompanied by an oxidation and reduction, i.e., by a change in oxidation state. Thus, both separants are continuously flowing towards both electrodes as they are interchanged between the forms in which they are present.

Without the particular system of carrier-formers employed in this invention that allows for reflux, little, if any, separation would occur since both separants would end up at the same electrode. However, the carrier-formers used herein are selected so that the exchange favors the net movement of one separant toward one electrode and the net movement of the other separant toward the other electrode. That is, the affinities of the carrier-formers for the separants plus any basic difference in oxidation potential in oxidation reactions, if any, is such that the net or overall movement of each separant is in a direction opposite to that for the other separant. The most oxidized form of each separant, e.g., the ferric form of iron, has a net flux toward the cathode and the least oxidized form, e.g., the ferrous form of iron, has a net flow toward the anode so that reduction can be effected by the cathode and so that oxidation can be effected by the anode. This oxidation and reduction propagates throughout the length of the cell resulting in the separation of the separants.

To maximize separation, and optimize power usage, refluxing should be induced at or near the electrodes. Reduction of the most oxidized forms of the separants is normally initiated at the cathode. This change in oxidation state is accompanied by a change in separant form and by a change in the net direction of movement so that the formerly oxidized form of the separant is given a net movement away from the cathode after reduction for further interaction and exchange as previously described. A similar reaction, although an oxidation, occurs at the anode to change the oxidation state, the form and the direction of the reduced form of the separants.

When the desired degree of enrichment or separation has been produced, the product separants can be withdrawn. The products may be withdrawn after deposition onto one of the electrodes or directly from solution. If the latter method is employed, no flow greater than that necessary to remove product is required.

A net movement of the most oxidized form of each separant toward the cathode and of the least oxidized form of each separant toward the anode can be accomplished in several ways. Most simply, if the uncomplexed separants are cations in solutiion, it can be accomplished by using a sufficient quantity of a single anionic ligand as the carrier-former if such material has a greater affinity for or reacts to produce the least oxidized form of the separants. If the reaction is electron exchange, this type of carrier-former unites with each separant in its lower oxidation number form to form separant-carriers having an opposite charge and moving in a direction opposite to that of the simple separant ions themselves or the set of separant-carriers formed from the higher oxidation state. An anionic carrier-former having a stronger affinity for or reacting to become the least oxidized form of the separant will form one or more separant-carriers with the least oxidized form such that the least oxidized form of the separant is given a net movement toward the anode. Since movement of the least oxidized form of a separant toward the anode is determined by the average weighted velocity of the various separant-carriers in which it appears, a stronger affinity for the lower oxidation state in electron exchange reactions allows for a range of concentration of carrier-formers that reverses the direction of the lower oxidation state without reversing the migration direction of the higher oxidation state which is therefore left with a net movement toward the cathode.

Bromine in the form of bromide ions has been shown to be useful as a typical, single, carrier-forming material. For example, it can be advantageously employed as the single carrier-former when separating or purifying copper and/or iron.

The use of a single, negative, carrier-forming material is presently limited when used to give the preferred directions in electron exchange reactions since most presently-known, negative ligands have a greater affinity for the most oxidized form of the separant. Nevertheless, these ligands can be employed as carrier-formers when separating separants which carry a positive charge in solution by using them in combination with ligands which carry a neutral or positive charge and which exhibit a greater affinity for the higher oxidized form of a separant than do the negative ligands. When used in this manner, the negative ligands attached to the most oxidized form of a separant are, in effect, displaced, so that they, in effect, show a greater affinity for the lesser oxidized form of the separant. In this case, each separant is present in the following separant-carrier forms: as the separant ion itself in its initial or uncombined form; as a complex combined with the positive or neutral ligand, and as a complex combined with the negative ligand. For electron exchange, a separant migrates with a velocity and direction that is determined by the average migration velocity of all of the above species. However, because of the greater affinity of the neutral or positive carrier-formers for the higher-oxidized form of the separant, the latter is given a net movement toward the cathode and the least oxidized form of the separant is given a net movement toward the anode.

When a neutral or positive ligand is to be employed to compete with the negative ligands which prefer the higher oxidized form of a separant, it is preferable to employ positive ligands. This preference is based upon the reinforcement provided by positive ligands to the natural movement of the positive, higher oxidized state of the separant toward the cathode. By comparison, a neutral ligand can increase the natural movement of a positive separant toward the cathode only if it reduces the viscosity for migration.

Neutral ligands having a greater affinity for the higher oxidized form of the separant include, for example, mono-, di- and tri-ethanolamine, morpholine, and amino acids in slightly acid media. Suitable positive ligands include, for example, quaternary ammonium salts such as trimethylammonium ethyl-amino-ethyl ether chloride and other ammoniated compounds having a positive charge on one end and a chelating group on the other end, such as ammoniated chlorophyl hydrochloride.

Figure 2:
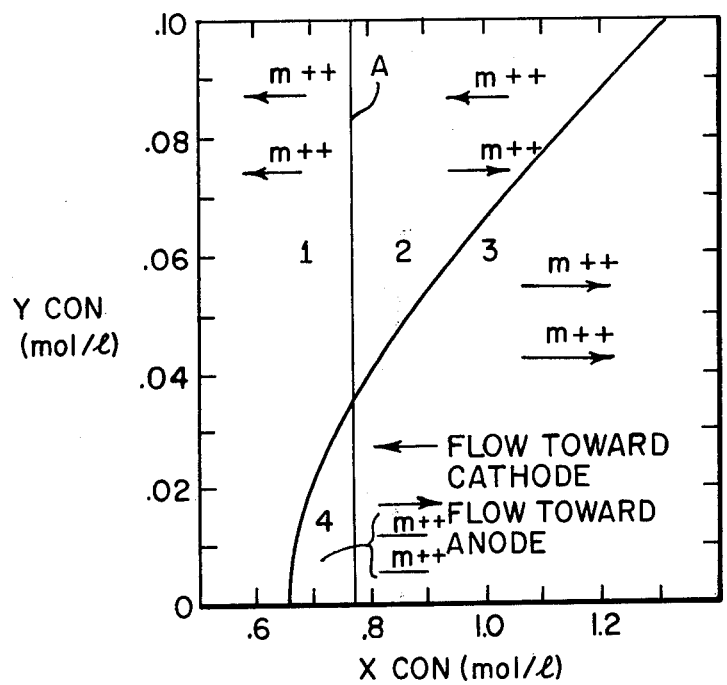
FIG. 2 is a graphical representation of the isoelectric locus for each of two oxidation states of a particular separant (m) using a particular pair of ligands, (Y and X−) and illustrates the selection of ligand concentrations which produce counterflow of the oxidation states of the separant and which permit reflux of the separants.

When employing an electron exchange between separantcarriers using the aforedescribed combined carrier-formers (negative and positive or neutral ligands), it has been found that satisfactory results are not always obtained at all concentrations of each of the ligands. Instead, separation is obtained only when the concentrations of the ligands lie within a particular working range. This working range is limited or bounded by the isoelectric points of the separants with the particular ligand set and it can be calculated from experimentally-determined, stability-constant data for the ligands in the particular solvent employed. THe isoelectric locus for each oxidation state of a separation can be plotted as shown by way of example in FIG. 2 which illustrates the isoelectric point curves (A and B) in water for a pair of ligands, $X^-$ (negative) and Y (neutral), used to create a separant-carrier pair from the two oxidation states $m^{3+}$ and $m^{2+}$ of the separant m. The boundary line A in FIG. 2 represents a stagnation or zero transport condition for the separant m in its lower oxidation state $m^{2+}$. A change in the concentration of ligand $X^-$ from its value along this line (graphed as a shift to the left or right of A), produces a transport of $m^{2+}$ toward one of the electrodes. For example, an increase of ligand $X^-$ concentration from its A value, produces a net movement of $m^{2+}$ toward the anode whereas a decrease in the concentration of $X^-$ from this value produces a net movement of $m^{2+}$ toward the cathode. The former is necessary to permit refluxing in the preferred direction, since it is only the lower oxidized form of the separant that can be oxidized and reversed in direction as it moves toward the anode. Similarly, boundary curve B represents the stagnation or zero transport curve for the higher oxidation state of the separant, $m^{3+}$. Upon superimposing these curves (A and B) on each other as shown in FIG. 2, it is seen that in both zones 1 and 3, defined by these boundary curves, the net or overall migration direction for both carriers is in the same direction although that direction is opposite for these two zones. Therefore, when operating at ligand concentrations within zones 1 and 3, there is no reflux.

In zone 4, the carrier pair travel in opposite directions, but counter to the normal flow of oxidation with the oxidized form of the separant migrating toward the anode and the reduced form migrating toward the cathode. Since oxidation and reduction by the end electrodes are precluded, refluxing cannot occur under these conditions. The proper operating zone is zone 2 in which the separant in the $m^{3+}$ state travels toward the cathode so it can be reduced to the $m^{2+}$ state (and reversed) and the separant in the $m^{2+}$ state travels toward the anode so it can be oxidized to the $m^{3+}$ state (and reversed).

A similar plot must be made for each separant for the same set of ligands to ascertain the operating conditions. Since it is necessary to have a carrier pair for each separant, the proper operating conditions lie within the region which is common to and lies entirely within zone 2 for each separant. A relatively large area of overlap of zone 2 is guaranteed for isotopes by their similarity.

For ligand exchange reactions in a system of more than one ligand, it is helpful to plot isoelectric point curves to determine a working zone as described for electron exchange reactions. If optimum operating conditions are to be employed, an isoelectric point curve is plotted for each separant. Although ligand concentrations on both sides of each curve may be effectively employed, the points between a resulting pair of curves represent ligand concentrations which provide optimum separation conditions. The distance between the isoelectric curves is a measure of the separation efficiency. If the plotted curves intersect for a separant pair, the intersection point conditions must not be selected since, at this point, for this separant pair, the aforementioned ratio of the flux ratios is equal to one, thereby preventing separation from occurring.

In a two-ligand system, substantial control can be exercised over the reflux ratio by changing the ligand concentrations within the operating zone. Such control derives from the fact that at one isoelectric boundary of the operating zone, the flux or drift velocity of one separant-carrier is zero whereas, at the other isoelectric boundary, the drift velocity of the other separant-carrier is zero. Between these isoelectric limits, any desired separant carrier reflux ratio between 0% and 100% can be obtained.

When setting the operating parameters for the process of this invention, it will be found that, in general, a compromise must be made between production rate, i.e., rate of movement of separants towards opposite electrodes, and purity of the products. This compromise situation exists because certain factors, e.g., operating temperature, increase with power consumption which increases reaction rates but decreases separation coefficients and increases back diffusion. Judicious adjustment of the operating temperature and selection of the solvent can materially improve the operation of this process.

Changes in solvents can be used to extend the operating temperature range to permit the use of high or low temperatures, to change the activity coefficients of the separants, and/or to alter the effectiveness of the ligands. For example, by choosing a solvent which is more acidic than water in the Lewis sense, e.g., acetic anhydride, weak basic ligands such as the bromide ion become more effective as well as the activity coefficients for separants and their associated rate constants for exchange reactions generally increase. Combinations of solvents may be employed to enhance the advantages and minimize the disadvantages associated with use of the solvents individually. For example, solvents which produce a large increase in separant activity coefficients but which do not permit the use of low operating temperatures, e.g., dimethyl sulfoxide and dimethyl formamide, may be employed in combination with solvents which permit the use of low operating temperatures but which do not particularly enhance separant activity coefficients, e.g., ethanol, liquid ammonia and liquid sulfur dioxide. This solvent combination permits the use of lower temperatures to obtain an enhanced separation ratio, together with decreased thermal diffusion without too large a loss in reaction rates associated with low temperature operation.

If it is necessary to employ relatively high operating temperatures, e.g., to increase reaction rates which are slow relative to the transit time of a long life-time separant-carrier, the solvent must be one which is substantially unaffected by the higher temperature and precautions must be taken to eliminate heat convection currents. The latter may be accomplished by the use of a packing material such as Fiberglas, asbestos or glass heads, or the use of a gel. In addition, pressurization may be used to prevent boiling. The need for increased operating temperature may be eliminated by or supplemented by the use of a catalyst. Presently-available ion-exchange resins may be advantageously employed as catalysts.

In some cases, the materials may be over-oxidized or over-reduced at the electrodes. When this occurs, the materials precipitate out of solution and can be removed as product. However, if excessive precipitation occurs, insufficient material will be left in solution to sustain the reflux which is necessary to produce the extreme separations made possible by this invention. Therefore, at least some of the precipitate must be returned to solution. This can be done by reversing the current flow or by employing periodic short rest periods; the percentage of the time devoted to resting is determined by the percentage of over-precipitation.

Over-reduction and over-oxidation problems may be eliminated by using auxiliary or interface electrodes to provide the oxidation-reduction function necessary for refluxing. Interface electrodes are boundaries within the electrolytic solution at which oxidation-reduction reactions occur between the interface electrode materials and the separant-carriers so that the separants are transferred from one carrier stream to the other for reflux in the central reaction zone. The separants are thereby prevented from reaching the physical electrodes.

In addition to eliminating over-oxidation and over-reduction at the physical electrodes, interface electrodes also make it possible to reverse the otherwise necessary requirement that the most oxidized separant have a net movement toward the cathode (for reduction) and that the least oxidized separant have a net movement toward the anode (for oxidation). This is done by performing the oxidation and reduction externally to the end electrodes, either chemically or electrically. Instead, with interface electrodes, the oxidized form of each separant may be given an overall movement toward the anode since the anode interface electrode can reduce and return the oxidized forms of separants for reflux. Likewise, the solution between the cathode and the cathode interface may be an oxidizing solution so that the reduced form is oxidized when it enters the interface. Negative ligands having a preference for the most-oxidized form of the separant can then be employed without using positive or neutral ligands to block their preference for the most-oxidized forms of the separants, as previously described. A further advantage obtainable when using interface electrodes is that the oxidation-reduction function can be performed externally to the cell and solution brought in through side channels, thereby decreasing the required cell size. Any resulting fluid flow within the cell can be damped out by packing in the same way as for convection currents. The only function left to the physical electrodes is the one of supplying the motive force to cause movement of the carriers.

Interface electrodes can be made by employing materials with an oxidation potential that places them between the physical electrodes and separants. The materials employed to form the interface electrodes are selected on the basis of their oxidation potential and their ability to form carrier pairs with the given solvent ligand system. The interface electrode materials must not react with the separants or carrier-formers in a manner which would remove any of these materials from the process. Because interface electrodes can change the direction of oxidation flow, they will be referred to as oxidizing and reducing interfaces rather than specifically as cathode and anode interfaces. Materials which can be employed to form oxidizing interface electrodes include, for example, iron, nickel or cobalt. Tin is a good reducing interface electrode material since the stannous to stannic couple is easy to oxidize and stannic will oxidize tin that plates out on the cathode. Some materials, e.g., the cuprous-cupric couple, can be employed as either oxidizing or reducing interface electrode materials, depending on their oxidation potential relation to the separants, i.e., ferrous-ferric<cuprous-cupric<stannous-stannic<$V^{++} - V^{+++}$. Similarly, $K^+$ and $Zn^{++}$, respectively, form good reducing and oxidizing interface electrode materials in non-electron exchange reactions.

Figure 3:
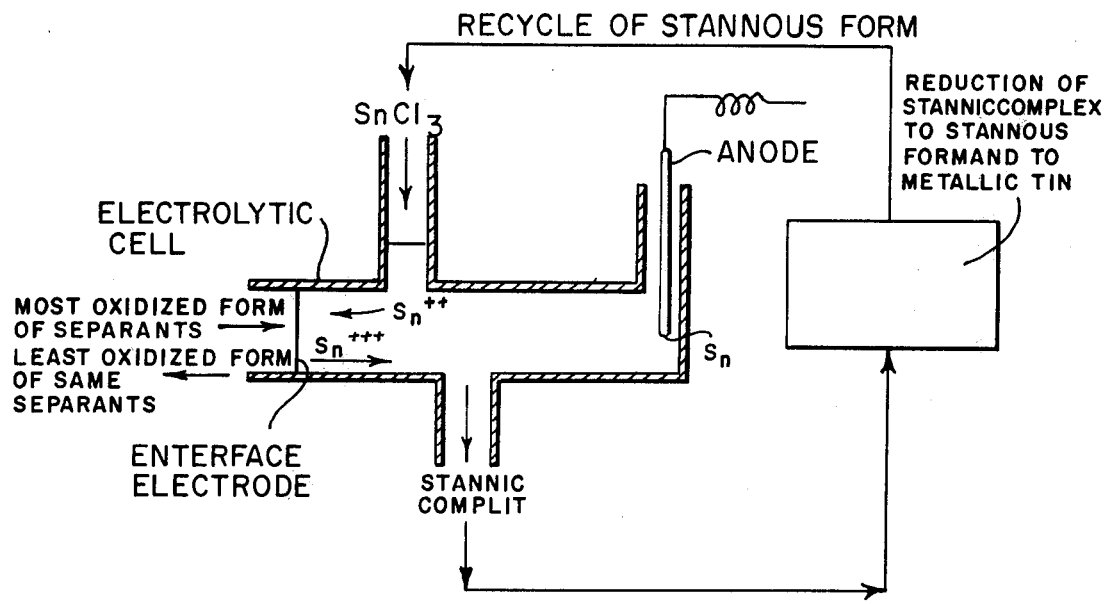
FIG. 3 is a partial sectional view of the anodic end of an electrolytic cell showing the formation of an interface electrode as an alternative method for providing the required separant flux reversal in this invention.

By way of example, if tin is the material selected to form the reducing interface electrode at the anode end, it is introduced into the electrolytic cell in its stannous form at a point near the anode as shown in FIG. 3. The stannous tin begins to migrate toward the cathode due to its positive charge as soon as it enters the electrolytic cell. In the course of its migration, it encounters oxidized forms of the separants which, in this example, flow toward the anode, and reduces the separants to their reduced forms, thereby transferring the separants from their oxidized to their reduced forms and reversing the flow direction of the separants. At the same time, the stannous tin is oxidized to its complexed stannic form and is reversed in direction.

Under equilibrium conditions, a stationary boundary or interface will exist at which stannous tin is oxidized to stannic tin and at which the oxidized form of the separants are reduced and reversed in direction. The stannic form can be withdrawn near the anode, reduced externally to the cell to both the stannous form and metallic tin, and returned to the cell for further interface electrode use. The anode material would be metallic tin which would oxidize and be dissolved. In a similar manner, an oxidizing interface electrode can be formed near the physical cathode using dichromate ion to oxidize and reverse the least oxidized forms of the separants.

The interface electrode remains stationary as long as cell operating conditions remain constant. However, if, for example, the separant concentration changes so that there is a reduction in the amount of most oxidized separant, the reducing interface electrode will move towards the center until a new equilibrium position is reached. Thus, it will be understood that the position of the interface electrodes can be controlled by controlling the concentration of the interface electrode material and separants. When carrying out this process in a gel, heat may also be used to control the interface positions by altering the equilibrium constant.

Figure 4:
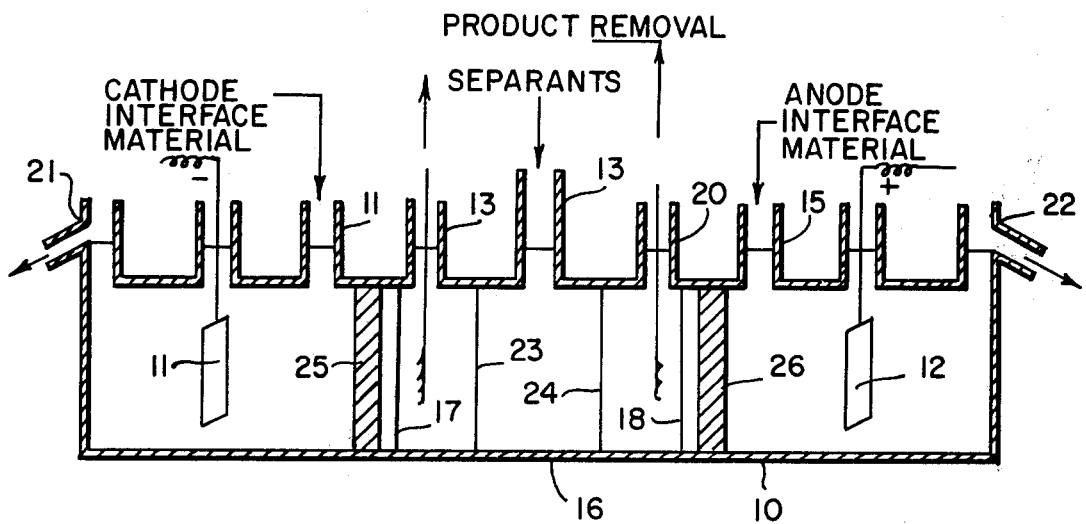
FIG. 4 is a cross-sectional view of an electrolytic cell taken along the cell's length showing one method of feeding separants into the cell and showing the formation of interface electrodes and the dampening of fluid movement within the cell's separation zone.

As earlier described, electrolytic solution flow should be minimized. To prevent significant solution flow from occurring when interface electrode material (or any other material) is being added to and removed from the electrolytic cell, material capable of dampening out solution movement is placed in the cell on the physical electrode side of the interface electrodes as shown in FIG. 4. In FIG. 4, the numeral 10 designates an electrolytic cell in which there are a pair of physical electrodes 11, 12 positioned adjacent the ends of the electrolytic cell. The separants are added to the electrolytic cell 10 through an intermediately-positioned feed tube 13. Interface electrode solutions are added through tubes 14, 15 positioned intermediate the central feed tube 13 and the physical electrodes 11, 12. Flow of the entering interface electrode materials is away from the nearest physical electrode and toward a separation zone 16 in the center of the electrolytic cell 10. As the interface electrode materials flow toward the separation zone 16, they encounter and react with counterflowing carrier streams of the separants, as previously described, with the result that interface electrodes 17, 18 are produced adjacent the separation zone 16. The products may be removed in several ways including, for example, removal though capillary tubes 19, 20 which extend into the electrolytic cell 10 between the interface electrodes 17, 18 and the separant feed tube 13 and which produce minimum disturbance. The spent interface material is shown being removed by overflow into end exit tubes 21, 22. The separation zone 16 may contain visible separation interfaces 23, 24 which will be more particularly described hereafter.

The aforedescribed inflow and outflow of materials may produce significant flow which may adversely affect the operation of this process. To substantially reduce such flow, porous plugs 25, 26 may be positioned within the electrolytic cell 10 between the interface electrodes 17, 18 and the interface electrode inlet tubes 14, 15, respectively. The porous plugs 25, 26, rather than being separate as shown in FIG. 4, may be a continuation of of packing material (not shown) which may be employed throughout the entire separation zone 16.

As previously described, refluxing is maintained by oxidation and reduction at or near the electrodes. However, in any process, oxidation and reduction are accompanied by a one-way movement of the carrier-forming ligand material itself so that it eventually ends up at one of the electrodes. Therefore, ligand material must be continuously added, e.g., at one electrode, and removed, e.g., at the other electrode. This can be accomplished in several ways. For example, ligand material may be supplied and removed through side vents in the electrolytic cell and passed through interface electrodes employed to retain the separants therebetween. Reversible electrodes can also be used to supply the ligand material. For example, if the ligands are halide ions, by making both physical electrodes from a metal, such as copper, silver, lead or mercury which form insoluble halides, and packing the cathode with that particular halide salt of the electrode metal, halide ions are released at the cathode as the salt is reduced and flow toward the anode where they recombine with the oxidized anode material. When the cathode is exhausted of insoluble salt, the electrodes are disconnected, flushed, interchanged in position and reconnected so that the electrodes are renewed. The use of interface electrodes will isolate the physical electrode reactants from the separants so that the switching operation will not disturb cell operation.

Reversible electrodes can also be formed from ligands that are insoluble in their acid form, such as salicylic acid in water. The reduction of the hydrogen ions at the cathode brings the ligand ions into solution where they migrate to the anode. Hydrogen ions produced at the anode by the oxidation of water reprecipitates the ligand in its acid form. In cases where the insoluble form of the ligand is soluble in another solvent that is immiscible with the electrolytic solvent, an auxiliary channel communicating with both ends of the cell and containing the other solvent can be employed to return the ligand material to the electrode from which it started. The return flow can result from forced circulation or by natural diffusion. For example, bromine ($Br_2$) from bromide ion oxidation can be returned via a carbon tetrachloride channel where water is the electrolyte solvent. Again, materials such as porous plugs, can be placed within the cell to dampen out any fluid motion.

In addition to the ligand transport, there will also be transport of any auxiliary ions that accompany the ligand to maintain ionic neutrality. These ions too will have to be supplied and removed in a direction opposite to that of the ligand supply. For example, if Ag-AgBr electrodes supply the flow of $Br^-$, a second anode of zinc can supply a counter-flow of $Zn^{++}$, which is removed by plating metallic zinc onto a second cathode. The current to the two electrode pairs is divided proportionally to the respective transference of $Zn^{++}$ and $Br^-$ and the proper proportionality is maintained by adjusting the current to keep the $Zn^{++}$ and $Br^-$ concentrations constant.

The separation of separants which exhibit a negative or neutral charge in solution is substantially the same as described for separants having a positive charge in solution. Preferably, the most oxidized form of each separant is directed toward the cathode and the least oxidized form is allowed to move toward the anode. With both negatively-charged and neutral separants (in solution), the carrier-formers are capable of reacting with the separants to form both positively-charged and negatively-charged separant-carriers. When interface electrodes are employed, the above-described normal directional movements may be reversed. When separating neutral separants, at least two carrier-formers of opposite charge must be employed.

The process of this invention can be carried out in a very small electrolytic cell having an electrode to electrode distance of only a few millimeters, so that the only limit on the smallness of the cell employed is the manufacturer's ability to make it small. The small cell size that can be employed follows from the short distance in which separation occurs which can be shown mathematically as follows. In a two-separant system described by equation (1), the variation of a particular separant concentration with distance along the electrolytic cell can be determined from material conservation laws. For Cm it is:

$$\frac{\partial y}{\partial x} = \frac{1}{V}[k_+(ry-t)(C-y) - k_-y(c+t-ry)], \quad (2)$$

where
y = concentration of Cm
V = average drift velocity of Cm,
$k_+$ and $k_-$ = forward and reverse rate constants for exchange according to equation (1),
r = $V/V_{Am}$
t = (the transport of m)/$V_{Am}$
c = concentration of Cm+Cn,
c = concentration of Am+An
x = distance along cell from reference point $x_o$.
The equilibrium, i.e., t=co, solution of equation (2) is $$y/C - y = \exp[C(k_+ - k_-)X/V_{Am}] \quad (3)$$

In arriving at equation (3), thermal diffusion effects have been neglected since, for a first approximation, they have been observed to be too small to consider except for isotope separation. The diffusion effect will be discussed later when describing the transition interface thickness. Additionally, because migration velocities are so nearly the same, they have been assumed to be equal for equivalent separants and separant-carriers. For equation (3), the theoretical plate length (L) can be easily obtained for difficult separations, i.e., $k_+/k_-$ is near unity, i.e., is equal to $1+\epsilon$ where $\epsilon$ represents a small number. In this case, equate $1+\epsilon$ to exp $(C\epsilon k_- L/V) = 1 + C\epsilon k_- L/V \quad (4)$ to find the distance in which the concentration ratio should change by $(1+\epsilon)$, from which one gets $L = V/Ck_-. \quad (5)$ In a typical example, $V=10^{-3}$ cm/sec. in a field of 1 volt/cm, C=1 mole/liter ($10^3$ cc), and $k_- = 10^9$ per second per unit volume, which gives L a length of $1 \times 10^{-9}$ cm. Thus, in a cell length of one cm, there can be thousands of theoretical plates. Therefore, extreme separations or purity can be obtained in an extremely short distance which, in turn, means that relatively low power is needed to produce a substantially complete separation.

When performing the process of this invention, it has been observed that interfaces develop at positions intermediate the electrodes (FIG. 4). Shortly after starting the process of this invention, very thin interfaces form near the electrodes and gradually move toward the center of the cell. Usually, the initial interfaces split and this splitting continues until a final state stabilizes with two interfaces that would coalesce unless prevented from doing so by feed rate and product control as described hereafter.

The number of interfaces which form depends upon the number of separants and impurities which also are separated into anode and cathode seekers. These interfaces represent maximum concentration gradients. That is, with respect to a particular separant, there is substantially none of that separant on one side of the interface whereas there is a high concentration of that separant on the other side. If the equilibrium concentration of separants changes from 99% m to 99% n for the separation represented by equation (3), and if the values for the variables of equation (3) are the same as set forth above with $(k_+ - k_-) = 10^6$ per second, the transition distance (x) from equation (3) is equal to $10^{-5}$ cm. This short transition distance is observed as an abrupt interface.

It is believed that these interfaces are formed when separant moving in one direction is oxidized or reduced by separant moving in the opposite direction which is reduced or oxidized to thereby form a boundary between the two separants. The interfaces may move depending upon the relative amounts of separants on each side of the interfaces. That is, after an elapsed time sufficient for the interfaces to form and move away from the electrodes, the ray material is input between the interfaces at a rate that balances material removal at the ends, which in turn is withdrawn at a rate that holds the interfaces within fixed position limits. As previously described, the initial interfaces will split and continue to do so until a final state stabilizes with two interfaces that would coalesce if the central feed were stopped and the current continued. However, the interfaces cannot be fully stabilized until the splitting phase has ceased. The working zone boundary for any particular division is selected during the splitting phase by fixing the position of the desired interface and letting the other drift away. This dichotomy is repeated until separation is completed. A single material may be isolated in two passes through the same type apparatus by setting the division on the immediate zone boundaries of the desired material, splitting first on, say, the anode-side boundary and the second time on the cathode-side boundary.

The position of the interfaces may be automatically controlled or stabilized if, e.g., the materials separated by the interface exhbit a difference in index of refraction or optical absorption. A Schlieren optical system can be employed to focus the interface image on a photosensitive detector so that a displacement of the image (caused by interface movement in the cell) causes a corresponding corrective change in the interface position by altering the flow of material into or out of the cell.

The width of an interface is limited by the diffusion taking place in the electrolyte. That is, diffusion opposes a concentration gradient and tends to remix the separants and tends to offset the transportation of species through the interface against the gradient. The separation limit set by diffusion can be determined by calculating the value for the characteristic length ($\lambda$) corresponding to an e-fold increase in separation or purification at the center of the interface. Assuming that the equivalent mobility is proportional to diffusion velocity, the diffusion ($F_d$) and electrical ($F_E$) fluxes for a separant m in a process as described by equation (1) are:

$$F_d = -D \, dm/dx \text{ moles/sec/cm}^2 \quad (6)$$

$$F_E = \frac{(Cm - Am)}{C + c} I/\gamma \quad (7)$$

Where
D = the average diffusion constant for the process
I = total current in faradays
$\gamma$ = ratio of separant particle flux in moles per second to the total current in faradays per second The maximum concentration gradient occurs at the 50 percent concentration point (half-way through interface). When there is zero transport, the value of $\lambda$ can be obtained by algebraically adding equations (6) and (7). The interesting case is when the separation factor $\epsilon$ is small. The solution is similar in form to that of equation (3); i.e., $$y/C - y) = \exp(x/\lambda), \quad (8.1)$$

for which $$y' = y(C - y)/C\lambda. \quad (8.2)$$

Since $\epsilon$ is small, only the first non-vanishing term will be retained. At $C = 2y$, equation (8.2) reduces to $$y' = y/2\lambda \text{ or } m' = m/2\lambda. \quad (8.3)$$

Also at the 50/50 point, [Cm] = [An] and [Cn] = [Am], which when substituted into the equilibrium equation $$[Cm]\cdot[An]/[Cn]\cdot[Am] = (1 + \epsilon/2)^2 \quad (9.1)$$

gives $$([Cm] - [Am])/(C + c) = \epsilon/8. \quad (9.2)$$

The particle current $I/\gamma$ is determined by the average mobility, the field strength, and the concentration; i.e., $$I/\gamma = 2\mu E m. \quad (10)$$

This then gives for the overall relation at zero transport $$Dm/2\lambda = 2\mu E m \epsilon/8, \text{ or } \lambda = 2D/\mu E \epsilon. \quad (11)$$

The stage length derives from its definition and is $$L = 2D/\mu E. \quad (12)$$

The energy per mole of separative work is the voltage drop, EL, times the current, $2\mu Em\gamma$, divided by the separative capacity, $\mu Em\epsilon^2/4$ moles per second. This gives $16D\gamma/\mu\epsilon^2$ faraday volts per mole of separative work. Typical values of $D/\mu$ and $\gamma$ are respectively fifty and two.

The formation of the interfaces will now be more specifically described with reference to a particularly clear example which is an initially mixed solution of iron and copper as separants with a bromide ion carrier-former system in aqueous solvent. Both the iron and copper appear in two oxidation states—ferrous and ferric for iron and cuprous and cupric for copper. This results in the formation of two interfaces in steady-state flow which represent an iron-copper/copper boundary on the reducing side and an iron/iron-copper boundary on the oxidizing side. Other boundaries may also form depending upon the impurities in the iron-copper feed. The copper-iron separation can be represented by the following chemical equation:

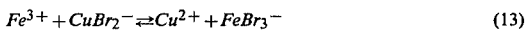

$$Fe^{3+} + CuBr_2^- \rightleftarrows Cu^{2+} + FeBr_3^- \quad (13)$$

There are other complexes of $Fe^{+++}$, $Fe^{++}$, $Cu^{++}$ and $Cu^+$, but all the exchange reactions have equivalent equations. As shown by equation (6), an oxidation or reduction of either the copper or iron is accompanied by a change in form, e.g., from one carrier form to the other, and by a change in direction resulting from the change from a positively charged separant-carrier to a negatively-charged separant-carrier.

The $CuBr_2^-$ and $FeBr_3^-$ separant-carriers migrate toward the anode whereas the ferric and cupric forms of the separants have an average migration toward the cathode in the working range of the bromide ion. In this example, the ferric ions are, in effect, deflected on their way to the cathode and prevented from reaching it by reaction with $CuBr_2^-$ according to equation (6) to reduce the iron to its ferrous state as $FeBr_3^-$ and thereby reverse the iron. Simultaneously, copper migrating toward the anode in its cuprous state ($CuBr_2^-$) is oxidized to $Cu^{2+}$ and turned toward the cathode. Cupric ions on the anode side of the iron-copper/copper interface and stray $FeBr_3^-$ ions on the cathode side of this interface are capable of passing through the reducing interface without change so that the copper concentrates on the cathode side and iron concentrates on the anode side of this interface.

The other interface (iron/iron-copper) forms between the iron-copper/copper interface and the anode and remains separated therefrom provided the separant feed to the cell at a point between these interfaces is sufficient. Otherwise, the two interfaces will merge into one. In ferric in in excess in the feed solution, the anode side interface arises from the exchange of bromide ions. That is, the more strongly oxidizing species of ferric ion will compete more strongly for bromide ions than cupric will.

This invention will now be further described by the following examples:

EXAMPLE 1

This example demonstrates the separation of iron from copper.

An aqueous solution of $Fe^{2+}$, $Fe^{3+}$ and $Cu^{2+}$ of about 0.2 molar total metallic ion content was brought to about 2.8 molar bromide by dissolving solid potassium bromide in the solution. The pH of the solution surrounding the cathode was adjusted to a pH between 1 and 2 with hydrochloric acid.

This solution was placed in a U-tube with graphite electrodes. The solution path length between electrodes was about 10 cm. A d.c. voltage of 4.5 volts was applied at the electrodes and this produced a current density of 0.1 amperes per square centimeter.

In this system in which water is a neutral ligand, the isoelectric points for copper are about 0.003 molar bromide for $Cu^+$ and about 4 molar bromide for $Cu^{2+}$ and the isoelectric points for iron are about 2.5 molar bromide for $Fe^{2+}$ and about 3 molar bromide for $Fe^{3+}$. Thus, the iron separation range lies entirely within the copper separation range which means that at 2.8 molar bromide, copper-iron separation should occur by the mechanism of this invention.

After ten minutes operating time, sufficient copper had plated out on the cathode to require removal from the cathode. This was accomplished by a 15-second current reversal. The copper broke away and was retained by a porous plug placed in the U-tube under the cathode until it redissolved. The current was reversed again and continued at the original magnitude. In about 20 minutes, an iron-free zone had developed near the cathode as visually indicated by the formation of an abrupt interface dividing a green zone from a brown zone. This system came to equilibrium after about 1.5 hours.

EXAMPLE 2

This example illustrates the use of interface electrodes and the separation of isotopes as well as of different elemental metals. It also illustrates the nonelectron or isoelectric stagnation separation of iron (ferrous) and copper.

An aqueous, iron (primarily ferrous) solution was made up containing: 0.23 molar $FeSO_4$; 0.004 molar $Fe_2(SO_4)_3$; 2.5 molar sodium bromide; and many impurities. A buffer solution containing materials capable of interacting with the iron and other ions to form interface electrodes was made up containing: 1.875 molar $Na_2SO_4$; 0.021 molar $H_2SO_4$; and 2.48 molar sodium bromide. The anode was copper and the cathode was CuBr-Cu.

These solutions were placed in a U-tube with the buffer solution in contact with the physical electrodes and with the ferrous solution positioned between the buffer solution and, thereby, isolated from the physical electrodes. The path length through the ferrous solution was 10 cm.

Forty minutes after initiation of current flow (70 milliamperes per square centimeter), interface electrodes formed at the boundaries between the ferrous and buffer solutions. The interface electrodes were observed as sharp boundaries. During the three hour operating period, the cathode interface electrode split once to allow the formation of a narrow band between the cathode buffer solution and the ferrous solution, while the anode interface electrode split twice to form two anode-side bands between the anode buffer solution and the ferrous solution zone. Analysis of the four bands (including the central band and three side bands) showed the following: copper was collecting in the cathode side band; the broad center band contained essentially unchanged starting material; the inside anode side band was collecting cobalt and nickel (impurities); and the outside anode side band was collecting cobalt, nickel, chromium, manganese, and a trace of iron that had been enriched in isotope $Fe^{57}$.

I claim:

1. A process for fractionating a mixture of difficult to separate dissolved materials of like ionic sign which may be all positive or all negative ions, where each of said materials to be separated will be refered to as a separant, comprising a solution containing said separants, one or more ligands that can combine with each said separant to form dissolved positively charged particles having the higher oxidation state called the oxidized state, and one or more additional ligands that can compete with said aforementioned ligands and combine with a portion of each said separants to form simultaneously dissolved negatively charged particles containing said separants in a lower oxidation state called the reduced state, where said dissolved ionic particles are known as separant-carriers, choosing said ligands such that the oxidation or reduction of a separant to its alternate oxidation state is accompanied by a sign change of its separant-carrier and such that there is for each said separant at least one separant-carrier that can react with at least one separant-carrier of opposite sign in each pair of positive and negative separant-carriers for each other said dissolved separant, where said pair is known as a separant pair, and simultaneously exchange oxidation state and sign in a time that is on the order of or shorter than the transit time of said separant-carriers through a theoretical plate based on a reaction time shorter than $10^{-7}$ seconds, placing said solution between two electrodes, the positive one known as the anode and the negative one known as the cathode, passing a current through the solution at a density insufficient to cause gross turbulence, which causes separant-carriers of opposite sign to course through each other in the process of ionic conduction, adjusting the concentration of said ligands to bring the transport of unseparated separants partitioned into carrier pairs to as near zero as practicable forming a quasi-isoelectric point, refluxing said separants transported by individual separant-carrier conduction by trapping them in a closed circuit reflux zone by oxidizing negative separant-carriers that enter an anode compartment into positive separant-carriers and by reducing positive separant-carriers that enter a cathode compartment into negative separant-carriers, inducing said oxidation/reduction by the direct anode/cathode electron reactions, holding said solution of separants in a steady state reflux until they have approximately reached equilibrium at which time the solution at the ends of the reflux zone will have reached a maximum of composition disproportionation and will be the maximum separation for the given voltage drop across the reflux zone.

2. The process of claim 1 in which the oxidation/reduction in the anode/cathode compartment is induced not by direct electrode contact but at an interface electrode comprising an interface between the solution containing said separants and a buffer electrolyte separating said separants from direct contact with the electrodes where said anode/cathode buffer contains a material of ionic sign similar to the separants that when in its oxidized/reduced form is a stronger oxidizing/reducing agent that any oxidized/reduced separant and said buffer material in the anode/cathode compartment has the same properties as said separants when reacted with the carrier forming ligands used for said separants, hereafter known as carrier-formers, i.e. the oxidized/reduced state having a positive/negative charge, oxidizing/reducing said anode/cathode buffer material externally and flushing the oxidized/reduced buffer electrolyte through the anode/cathode compartment or by direct anode/cathode reactions and flushing the anode/cathode compartment with the anode/cathode buffer electrolyte to maintain the concentration of the higher/lower oxidation state carrier-formers, where said interface electrodes form oxidation-reduction boundaries containing said dissolved separants in a reflux zone and the integrity of said interface electrodes and said reflux zone is maintained by the passage of current between the anode and the cathode.

3. The process of claim 2 in which the zero transport state for the reflux zone is automatically maintained by flushing the anode/cathode compartment with an anode/cathode buffer at its quasi-isoelectric point comprised of said buffer material and carrier-formers common to said refluxing zone having a carrier-former concentration that makes the transport of the oxidized form of said anode/cathode buffer material equal and opposite to the transport of the reduced form of said anode/cathode buffer material plus to minus a very small amount of one or more of said common carrier-formers as needed to maintain control of the position of said interface electrodes within operational limits, bringing said reflux zone, if not originally at the zero transport concentration, to the quasi-isoelectric point by continuous refluxing between said quasi-isoelectric anode and cathode buffers.

4. The process of claim 3 where it is operated as a continuous separation process comprised of separants in their initally mixed state in solution at approximately their quasi-isoelectric carrier-former concentration being introduced at a central point in the reflux zone and near-equilibrium separation products of reflux being removed at points within said reflux zone near said anode and cathode interface electrodes.

5. The process of of claim 4 where the higher oxidation state separant-carriers and buffer-carriers have a negative charge and the reduced state separant-carriers and buffer-carriers have a positive charge, and the reduction/oxidation of separant-carriers in the reflux zone is done at the anode/cathode end interface electrode by buffer electrolytes, the reduction/oxidation of said anode/cathode buffer electrolyte being done externally and used in excess to flush the anode/cathode compartment, said anode/cathode buffer being introduced at a point in said anode/cathode compartment near said anode/cathode interface electrode and allowed to overflow at a point in said anode/cathode compartment distant from said anode/cathode end interface electrode, the excess being sufficiently excess to the amount needed to obtain reduction/oxidation at said anode/cathode end interface electrode to offset the additional oxidation/reduction induced by the anode/cathode reactions, where the anode/cathode buffer material in its reduced/oxidized form is a stronger reducing/oxidizing agent than any separant in its reduced/oxidized form.

6. The process of claim 4 where the separants are nonionic, i.e. having zero ionic charge in their noncombined form, and where at least one of the carrier-forming ligands is a positive ion and at least one additional carrier-forming ligand is a negative ion, where the positive ion attaches to the nonionic separants to form positive separant-carriers and the negative ion attaches to the nonionic separants to form negative separant-carriers, with the buffer materials for the buffer electrolyte also being nonionic and also forming positive and negative carriers with said positive and negative ions.

* * * * *